(12) United States Patent  
Kurata

(10) Patent No.: US 7,456,947 B2  
(45) Date of Patent: Nov. 25, 2008

(54) INSPECTING APPARATUS AND INSPECTING METHOD

(75) Inventor: Shunsuke Kurata, Kamiina-gun (JP)

(73) Assignee: Olympus Corporation, Tokyo (JP)

( * ) Notice: Subject to any disclaimer, the term of this patent is extended or adjusted under 35 U.S.C. 154(b) by 353 days.

(21) Appl. No.: 11/078,084

(22) Filed: Mar. 11, 2005

(65) Prior Publication Data

US 2005/0206885 A1    Sep. 22, 2005

(30) Foreign Application Priority Data

Mar. 17, 2004    (JP)    ............ P 2004-076267

(51) Int. Cl.
    G01N 21/00    (2006.01)
(52) U.S. Cl. ............... 356/237.2; 356/237.1
(58) Field of Classification Search .......... 356/237.2, 356/399–401
    See application file for complete search history.

(56) References Cited

U.S. PATENT DOCUMENTS

| | | | | |
|---|---|---|---|---|
| 3,565,512 A | * | 2/1971 | Peck | ............. 359/656 |
| 3,721,827 A | * | 3/1973 | Reinheimer | ............. 250/201.3 |
| 4,503,555 A | * | 3/1985 | Brimhall et al. | ............. 382/109 |
| 4,577,141 A | * | 3/1986 | Saiki et al. | ............. 318/590 |
| 4,695,137 A | * | 9/1987 | Jorgens et al. | ............. 359/383 |
| 4,725,720 A | * | 2/1988 | Sawada et al. | ............. 250/201.3 |
| 4,919,001 A | * | 4/1990 | Ogiwara et al. | ............. 74/10.52 |
| 4,999,496 A | * | 3/1991 | Shaw et al. | ............. 250/310 |
| 5,276,550 A | * | 1/1994 | Kojima | ............. 359/368 |
| 5,557,456 A | * | 9/1996 | Garner et al. | ............. 359/393 |
| 5,818,637 A | * | 10/1998 | Hoover et al. | ............. 359/381 |
| 6,248,988 B1 | * | 6/2001 | Krantz | ............. 250/201.3 |
| 6,798,498 B2 | * | 9/2004 | Abe et al. | ............. 356/30 |
| 6,906,858 B2 | * | 6/2005 | Karaki et al. | ............. 359/383 |
| 6,909,540 B2 | * | 6/2005 | Engelhardt et al. | ............. 359/379 |
| 6,989,927 B2 | * | 1/2006 | Bonaventura | ............. 359/391 |

FOREIGN PATENT DOCUMENTS

| | | |
|---|---|---|
| CN | 1379459 A | 11/2002 |
| JP | 2001-134760 A | 5/2001 |
| JP | 2001-332595 A | 11/2001 |

\* cited by examiner

*Primary Examiner*—L. G. Lauchman  
*Assistant Examiner*—Jarreas C Underwood  
(74) *Attorney, Agent, or Firm*—Frishauf, Holtz, Goodman & Chick, P.C.

(57) ABSTRACT

An inspecting apparatus for inspecting a substrate includes an objective lens attaching part equipped with a plurality of objective lenses each having a different working distance (WD), an objective lens exchanging device which exchanges the objective lens, and a loading stage which is opposed to the objective lens and on which the substrate S is loaded. An objective lens detecting device detects the WD of the objective lens. Displacing devices relatively displace the objective lens and the loading stage in the direction of the optical axis of an inspecting light path and a direction rectangular to the optical axis. And a displacement controlling device controls the relative displacement of the objective lens and the loading stage in the direction rectangular to the optical axis when the lens detecting device detects that the WD of the objective lens is shorter than a predetermined WD.

10 Claims, 4 Drawing Sheets

INSPECTING APPARATUS AND INSPECTING METHOD

BACKGROUND OF THE INVENTION

1. Field of the Invention

The present invention relates to an inspecting apparatus which magnifies and is used to inspect substrates of semiconductor devices, such as those of a semiconductor wafer and a liquid crystal.

Priority is claimed on Japanese Patent Application No. 2004-076267, filed Mar. 17, 2004, the content of which is incorporated herein by reference.

2. Description of Related Art

In forming a device pattern on a surface of a semiconductor device, when manufacturing a semiconductor device, defects such as adhesion of foreign substances, and defects in pattern and abnormalities in size, may occur, and hence it is necessary to identify the defects. Concretely, visual examination is performed on the entirely substrate, and inspections using a line sensor are conducted, and a defective part is detected. An inspecting apparatus (observing apparatus) equipped with a function which performs a magnifying inspection of the surface of a semiconductor wafer is used for identifying these defects.

Plural objective lenses, each having a different magnifying power, are disposed in the inspecting apparatus. In the case in which magnifying inspection of the circuit pattern formed on the surface of a semiconductor wafer is performed, an arbitrary objective lens is inserted into an inspection light path, and is located opposed to the inspection location of the surface of the semiconductor wafer. Here, because the focal length of an objective lens decreases as the magnifying power of the objective lens increases, in the case in which the objective lens having a high magnifying power is used, the space between the objective lens and the semiconductor wafer must be decreased. That is, for example, in the case in which an observation at a high magnifying power and of a high resolution is performed using ultraviolet light for illumination, an objective lens for ultraviolet light is used, but the working distance (WD, free working distance) of this objective lens is only 0.2 to 0.3 mm. It should be noted that in changing the magnifying observation position of the semiconductor wafer surface, the objective lens is moved in the direction along the surface of the semiconductor wafer.

In addition, in the manufacturing process of a semiconductor device, cambering and bending of a semiconductor wafer occur. For this reason, when the objective lens is moved along the surface of the semiconductor wafer, the space between the objective lens and the semiconductor wafer may become narrower than the WD of the objective lens.

Therefore, as a conventional inspecting apparatus, for example, Japanese Unexamined Patent Application, First Publication No.2001-134760 discloses one which is equipped with distance sensors for measuring the distance from the objective lens to the semiconductor wafer, so as to maintain the space between the objective lens and the semiconductor wafer constant, in order to avoid contact of the objective lens with the semiconductor wafer.

Moreover, conventional inspecting apparatuses include one which is equipped with an entire surface chucking plate which performs vacuum chucking of the entire back surface of a semiconductor wafer as a loading stage on which a semiconductor wafer is disposed, such that the cambering of the semiconductor wafer and bending might be corrected using the vacuum chucking power.

SUMMARY OF THE INVENTION

The present invention provides the following.

That is, the first aspect of the present invention is an inspecting apparatus for inspecting a substrate by magnifying a surface of the substrate through an objective lens, including: a revolving nose piece equipped with a plurality of objective lenses each having differing WD (working distance), an objective lens switching device which actuates the revolving nose piece to switch the objective lens which is placed in the inspecting light path, a loading stage which is arranged opposed to the objective lens placed in the inspecting light path, on which the substrate is loaded so that the surface of the substrate crosses substantially rectangularly at an optical axis of the inspecting light path, an objective lens detecting device to determine the WD of the objective lens placed in the inspecting light path, a displacing device which displaces relatively the objective lens and the loading stage in the direction of the optical axis of the inspecting light path and the rectangular direction of the optical axis, and a displacement controlling device to control the relative displacement of the objective lens and the loading stage in the rectangular direction of the optical axis by the displacing the device when the lens detecting device detects an objective lens of which the WD is shorter than a predetermined WD (working distance).

In the inspecting apparatus of the first aspect of the present invention, the displacement controlling device may be one which limits the relative displacing range of the objective lens and the loading stage.

In the inspecting apparatus of the first aspect of the present invention, the displacement controlling device may be one which limits the relative displacing speed of the objective lens and the loading stage to a speed lower than a predetermined speed.

In the inspecting apparatus of the first aspect of the present invention, the displacement controlling device may be one which inhibits the relative displacement with the objective lens and the loading stage.

In the inspecting apparatus of the first aspect of the present invention, the displacement controlling device may be one which stores a cotrolling information which controls the displacement of the loading stage when an object lens having a short WD and possibility of causing an interference with the substrate is inserted in the inspecting light path.

In the inspecting apparatus of the first aspect of the present invention, the object lens attaching part may be a revolving nose piece which exchanges the objective lens by revolving it around the revolving axis.

In the inspecting apparatus of the first aspect of the present invention, the limiting of the relative displacing range may be limiting the inspecting area of the displacing area of the loading stage, based on the center position of the inspecting area which is displayed on the screen of the monitor when the objective lens to be inserted in the inspecting light path is exchanged with one having a WD (working distance) shorter than a predetermined WD (working distance).

In the inspecting apparatus of the first aspect of the present invention, the the displacing device may have both a high speed mode which is used when the inspecting is performed while displacing from one circuit pattern to the other circuit pattern, and a low speed mode which is used when the inspecting is performed while displacing in one circuit pattern.

In the inspecting apparatus of the first aspect of the present invention, the displacement controlling device may limit the displacement of the loading stage only to the displacement at the low speed mode.

The second aspect of the present invention is an inspecting method for a substrate by selecting suitably a plurality of objective lenses of which WD differs to perform magnifying inspection of the surface of the substrate, including:

a focusing step of relatively displacing the objective lens and the substrate in a direction of an optical axis of the objective lens which crosses substantially rectangularly at the surface of the substrate, such that the surface of the substrate is positioned at a focal point of the objective lens, and an inspecting point displacing step of relatively displacing the objective lens and the substrate in the rectangular direction of the optical axis, thereby changing the magnifying inspecting point on the surface of the substrate, wherein the relative displacement of the objective lens and the substrate in the inspecting point displacing step is controlled when the magnifying inspection of the substrate through the objective lens of which WD is shorter than a predetermined WD (working distance).

DETAILED DESCRIPTION OF THE INVENTION

Figure 1:
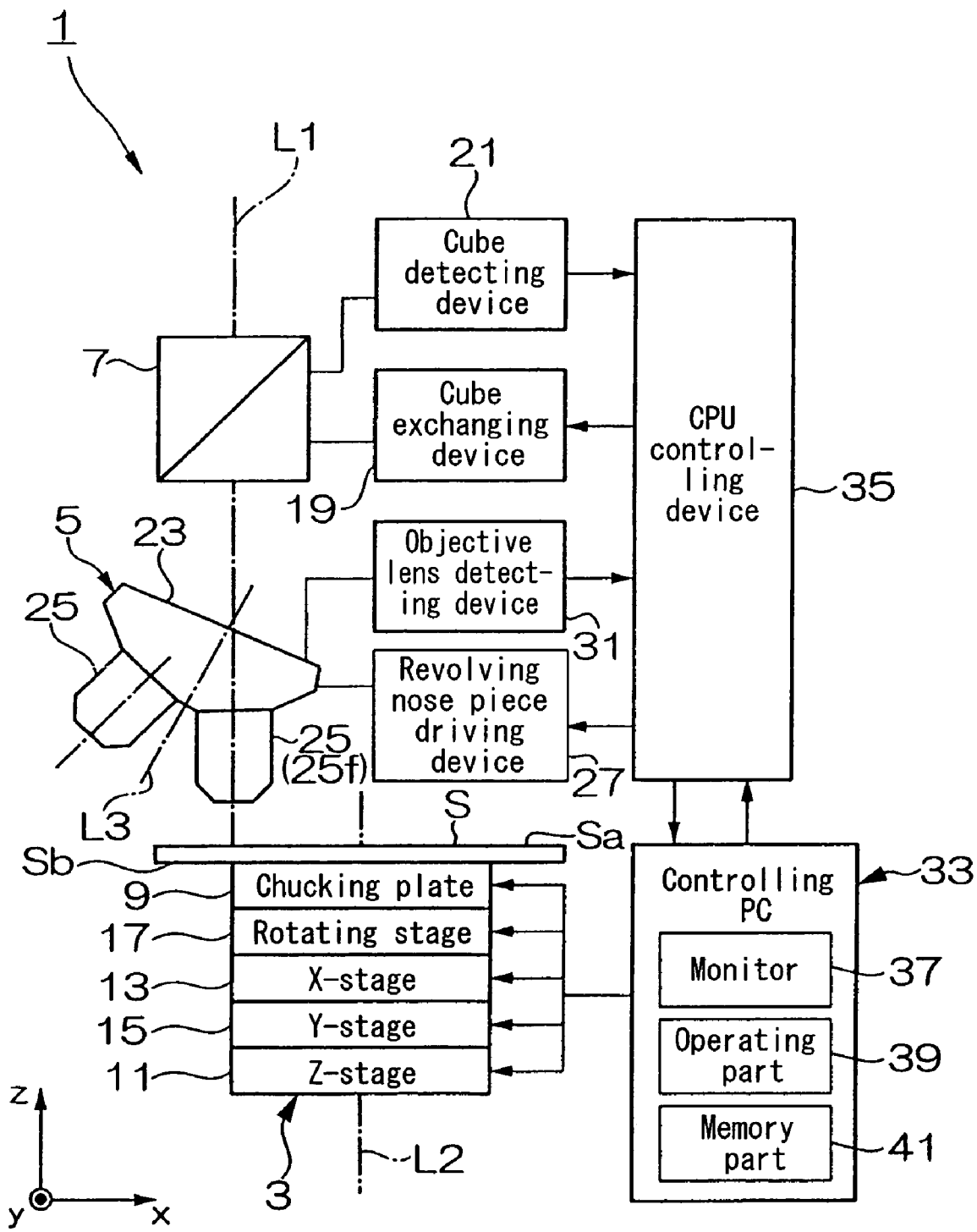
FIG. 1 is a side view showing the schematic constitution of the inspecting apparatus 1 in the first embodiment of the present invention.

FIGS. 1 to 4 show one embodiment of the present invention, and the embodiment explained here is one which is applied to a wafer inspecting apparatus which performs magnifying inspection of the defect of the pattern formed on the surface of a semiconductor wafer in this invention. As shown in FIG. 1, this inspecting apparatus (observing apparatus) 1 is equipped with a sample stage part 3, a revolving nose piece 5, and a filter unit 7, which were arranged sequentially in a direction of an optical axis L1 inspection light path through which ultraviolet light, or visible light for inspecting a surface Sa of a semiconductor wafer S and DUV passes.

It should be noted that, the visible light and ultraviolet light, which passed through the revolving nose piece 5 and the filter unit 7 sequentially, enter into an inspecting part (not shown), such as a CCD camera which photographs an image of an area which is inspected on the surface Sa of the semiconductor wafer S, and an eyepiece which looks at the inspecting area.

The sample stage 3 is equipped with an chucking plate (loading stage) 9 on which a semiconductor wafer S is loaded, a Z stage (displacing device) 11 which displaces the chucking plate 9 in the direction of an optical axis L1 (the direction of the Z-axis), an X stage (displacing device) 13 which displaces the chucking plate 9 to one way (the direction of the X-axis) which intersects perpendicularly in the optical axis L1 direction, a Y stage (displacing device) 15 which displaces the chucking plate 9 in the direction of Z-axis and the direction which intersects perpendicularly in the X-axis direction, and a rotating stage 17 which rotates the chucking plate 9 around the center axis line L2 along the Z-axis.

The chucking plate 9 holds the semiconductor wafer S by vacuum chucking, such that the surface of the semiconductor wafer S substantially rectangularly crosses the optical axis L1, when the semiconductor wafer S is loaded on the surface of the chucking plate 9. The surface of the chucking plate 9 which comes into contact with the semiconductor wafer S is smaller than the surface Sa of the semiconductor wafer S, and the chucking plate 9 holds a part of back surface Sb of the semiconductor wafer S by vacuum chucking.

The rotating stage 17 is one which adjusts the rotation position of the semiconductor wafer S, i.e., which serves to arrange the direction of the semiconductor wafer S to the inspecting apparatus 1 in the fixed direction based on an orientation flat or a notch.

The Z stage 11 changes the distance between the objective lens 25 which is disposed to the revolving nose piece 5 and the semiconductor wafer S, thereby matching the location of the surface Sa of the semiconductor wafer which is inspected with the focal point of the objective lens 25.

It should be noted that, although not illustrated here, the inspecting apparatus 1 is equipped with an autofocus (AF) mechanism, with which the operation of the Z stage 11 is controlled to detect the above focal point.

The X stage 13 and the Y stage 15 displace the location of the surface Sa of the semiconductor wafer S arranged in the inspecting light path, that is, which serve to change the location of the magnifying inspection area on the surface Sa of the semiconductor wafer S. Moreover, these X stage 13 and the Y stage 15 are constituted so that the chucking plate 9 can be displaced at two displacing speeds which consists of the high-speed mode at high speed, and a low-speed mode at a speed lower than the high-speed mode. Particularly, the high-speed mode is used when the area which is magnified and inspected is transferred from one circuit pattern to another circuit pattern on the semiconductor wafer S, and on the other hand, the low-speed mode is used when the magnifying inspection is performed with displacing it within the same circuit pattern.

The filter unit 7 is equipped with a plurality of kinds of filter cubes corresponding to the kind of light source used for inspecting or the inspecting method of the semiconductor wafer S, and an exchanging of the filter cube arranged in the inspecting light path is performed by the cube exchanging device 19. It should be noted that various filter cubes are attached to the circumference part of the cube attaching member (not shown) formed in the shape of a disk, and are inserted into and removed from the inspecting light path by rotating the cube attaching member. Moreover, the cube changing device 19 consists of an electric motor, for example.

As the above filter cube, for example, an ultraviolet light inspecting cube can be exemplified. Moreover, an inspecting method which uses visible light as a light source includes a clear vision field inspecting, a dark field inspecting, and differentiation interference inspecting, and for example there are a clear vision field cube, a dark field cube, and a differentiation interference cube as filter cubes corresponding to the inspecting methods, respectively.

A cube detecting device 21 is connected to the filter unit 7, thereby detecting the kind of filter cube disposed into the inspecting light path.

Figure 2:
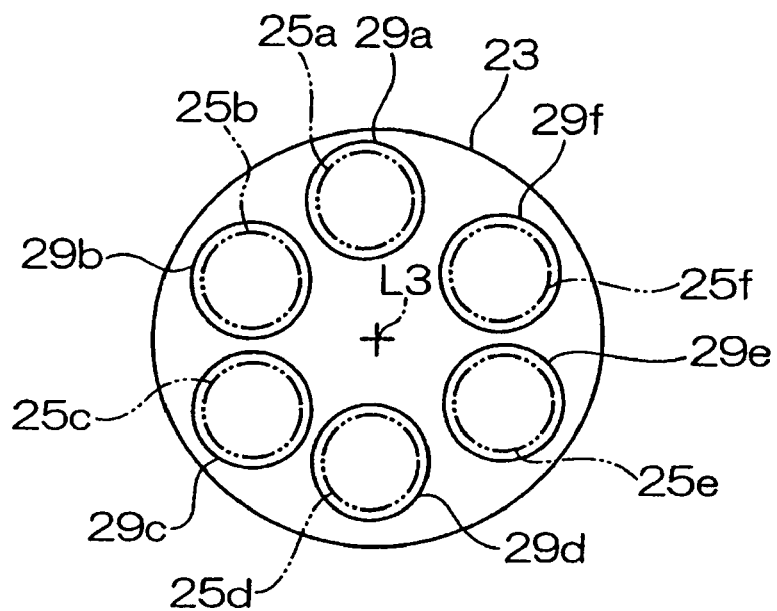
FIG. 2 is a plan view showing the schematic constitution of a revolving nose piece in the inspecting apparatus shown in FIG. 1.

The revolving nose piece 5 is equipped with a revolving nose piece main body 23 which can revolve around a revolving axis line L3, and a plurality of objective lenses 25 each of which magnifying power or WD differs attached to the revolving nose piece main body 23. The revolving nose piece main body 23 is constituted such that it revolves around the revolving axis line L3 by the revolving nose piece driving device (the objective lens exchanging device) 27 to insert a freely selected objective lens 25 into the inspecting light path. It should be noted that the revolving nose piece driving device 27 includes an electric motor, for example. The revolving nose piece main body is, as shown in FIG. 2, equipped with a plurality (six in the example shown in the drawing) of attaching parts 29a to 29f arranged evenly, to which the objective lenses 25 are detachably attached, respectively, around the revolving axis line L3.

Plural objective lenses 25 are attached to the attaching parts 29a to 29f of the revolving nose piece main body 23, respectively. That is, an objective lens 25a for visible light (referred to as a visible light objective lens 25a, hereinafter) having the lowest magnifying power is disposed to the attaching part 29a, whereas the objective lenses 25b to 25e are disposed to the attaching parts 29b to 29e, respectively, around the revolving axis line L3, such that the magnifying power of the objective lenses 25b to 25e becomes higher in the anticlockwise order. Moreover, the attaching part 29f disposed between two attaching parts 29a and 29e is equipped with an objective lens 25f for ultraviolet light (referred as an ultraviolet light objective lens 25f, hereinafter). It should be noted that, in general, the higher the magnifying power, the shorter the WD thereof, and the ultraviolet light objective lens 25f has a magnifying power which is higher than that of any of the visible light objective lenses 25a to 25e, and hence the WD (the space from the semiconductor wafer) of the ultraviolet light objective lens 25f is the lowest.

The data which correlate the attaching parts 29a to 29f to the magnifying powers and the kind of the objective lenses 25, respectively, are beforehand stored in the memory part of the control PC mentioned later. As shown in FIG. 1, an objective lens detecting device 31 is connected to the revolving nose piece 5, thereby constituting it so as to detect which attaching parts 29a to 29f is inserted into the inspecting light path. And the objective lens detecting device 31 is constituted such that the magnifying power, the kind, and the WD (working distance) of the objective lens 25 which is inserted into the inspecting light path can be detected based on the data stored in the above detection result and the above memory part. It should be noted that although in this embodiment the revolving nose piece 5 is exemplified, what is necessary is that a plural objective lenses can be exchanged, for example, an objective lens attaching part in which a plural objective lenses are attached to a member on which the plural objective lenses can be arranged linearly such that each of the plural objective lenses is exchanged by being slide, may be employed.

Moreover, the inspecting apparatus 1 is equipped with a CPU control device 35 for exchanging information mutually among the control PC 33 which controls operation of the sample stage part 3, the cube exchanging device 19, the revolving nose piece driving device 27, the control PC 33, the cube exchanging device 19, the cube detecting device 21, the revolving nose piece driving device 27, and the objective lens detecting device 31. And the control PC 33 is equipped with a monitor 37, an operating part 39, and a memory part 41.

The monitor 37 is one which displays various information as to the semiconductor wafer S. That is, on the screen of the monitor 37, as shown in FIG. 3, a main screen 37b which displays the image of the inspecting area on the semiconductor wafer S pictured by the CCD camera mentioned above, an wafer map 37d which indicates which circuit pattern the main screen 37b displays, and a shot map 37e which indicates which position in the circuit pattern the main screen 37b displays are displayed. Moreover, on this screen, an eight-direction-displacing-button 37f for displacing a circuit unit, a stepper unit, or the chucking plate 9 continuously in the X-axis direction and the Y-axis direction, and an information displaying area 37g which displays various information such as the magnifying power of the main screen 37b, coordinates, or the like, and various operation buttons for changing inspection results, magnifying power, or coordinates, are also displayed. Moreover, a displacing speed mode changing button 38 for exchanging the speed mode by which the chucking plate 9 is displaced by operation of the eight-direction-displacing-button 37f is also displayed.

The operating part 39 is equipped with a keyboard through which an operator of the inspecting apparatus inputs various information, a jog hand knob by which the chucking plate 9 is displaced in the X-axis direction and the Y-axis direction, and a mouse (neither is shown in the drawing) by which various information is inputted by clicking arbitrary locations on the screen of the monitor 37.

The information which is inputted through the keyboard involves change information, such as a change of the light source used for inspection and a change of the filter cube, and a change of the objective lens 25 inserted into the inspection light path. Therefore, for example, when the change information of the filter cube is inputted, the filter cube which is inserted into the inspecting light path is exchanged with the cube exchanging device 19 based on the change information and the detection result from the cube detecting device.

Moreover, for example, when an exchanging information of the objective lens 25 is input, the revolving nose piece driving device 27 exchanges the objective lens 25 which is inserted into inspecting light path based on the exchanging information and the detected result from the objective lens detecting device 31.

In addition, when an exchanging information of either the light source or the filter cube is inputted through the keyboard, the other exchanges of the light source, the filter cube, and the objective lens 25 are engagedly performed such that it should match with the contents of the exchanging information. That is, for example, when an information of exchanging the light source used for inspection from visible light to ultraviolet light is inputted, a cube for ultraviolet inspection is inserted into the inspection light path, and simultaneously an objective lens 25f for ultraviolet light inspection is inserted.

When the jog handle knob is operated, information to displace the chucking plate 9 in the direction of the X-axis and the direction of the Y-axis is outputted from the control PC 33 to the X stages 13 and the Y stage 15, corresponding to the operated direction. At this time, the inspecting area of the image displayed on the monitor 37 displaces in the direction in which the jog handle knob is operated. It should be noted that the displacement of the chucking plate 9 by operation of the jog handle knob can be performed at two kinds of displacing speed, i.e., a high-speed mode and a low-speed mode, and it can switch to either of the two modes by key operation of the keyboard. This switching of the speed mode is performed by, for example, arranging and clicking the pointer 37a displayed on the screen of the monitor 37 on the displacing speed mode switching button 38.

Figure 3A:
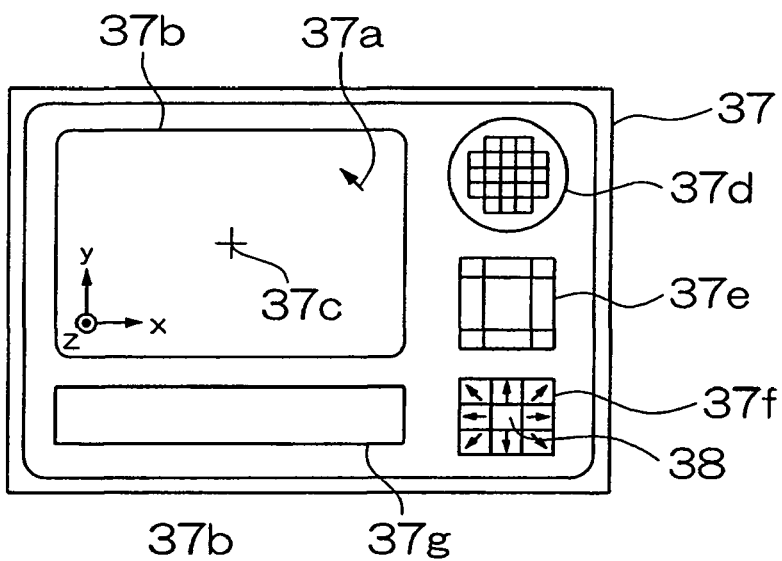
FIG. 3A is a figure showing the displaying state before click operation, in the inspecting area displayed on a monitor of the inspecting apparatus shown in FIG. 1.
Figure 3B:
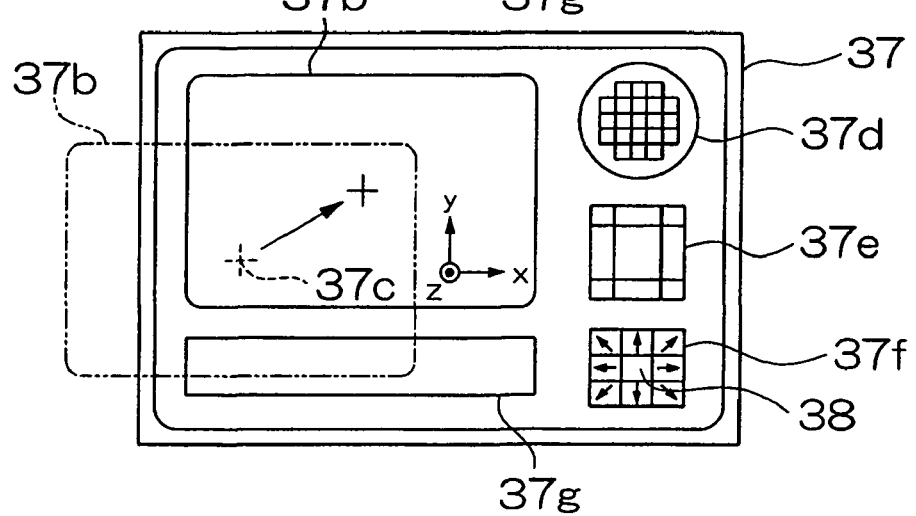
FIG. 3B is a figure showing the displaying state after click operation, in the inspecting area displayed on a monitor of the inspecting apparatus shown in FIG. 1.

As for the mouse, for example, the various buttons displayed on the screen of the monitor 37 can be clicked instead of the keyboard, thereby enabling to input a variety of information. Moreover, for example, the chucking plate 9 can be displaced instead of the jog handle knob. That is, as shown in FIG. 3A, when a pointer 37a displayed on the screen of the monitor 37 is arranged on a desired location in the inspecting area 37b of the semiconductor wafer and clicked, then, as shown in FIG. 3B, the chucking plate 9 will displace such that the above desired location should be located at a center 37c of the main screen 37b. Moreover, by arranging the pointer 37a on the predetermined location on the wafer map 37d and the shot map 37e and clicking it, the chucking plate 9 can be displaced similarly. Furthermore, by arranging the pointer 37a on the predetermined location on the eight-direction-displacing button 37f and clicking it, the chucking plate 9 can be displaced. It should be noted that, the displacement of the chucking plate 9 by clicking the mouse is performed in the mode of the speed beforehand set up with the displacing distance, the magnifying power, etc.

Moreover, the inspecting apparatus 1 is constituted such that the scanning operation, i.e., displacing the chucking plate 9 among a plurality of defects, can be performed, thereby displaying the defects dotted on the surface Sa of the semiconductor wafer S in the inspecting area on the main screen 37b of the monitor 37 sequentially, when the location coordinate of the defect on the semiconductor wafer S is known beforehand. The scanning operation is conducted by performing a predetermined operation in the operating part 39. It should be noted that the displacing of the chucking plate 9 accompanying the scanning operation is performed at the high-speed mode. Moreover, the displacing range of the chucking plate 9 in the scanning operation is the whole surface Sa of the semiconductor wafer S.

In the memory part (displacement controlling device) 41, controlling information is stored. The controlling information controls the displacement of the chucking plate 9 in the directions of the X-axis and the Y-axis, in the state where WD is short and the magnifying power is high, and the objective lens 25f for ultraviolet light which may cause an interference with the semiconductor wafer S is inserted into the inspecting light path.

This controlling information includes a prohibition of the scanning operation, a limitation of displacing range, and a limitation of displacing speed.

The limitation of displacing range indicates that the displacing range of the chucking plate 9 is limited to about ten times of the inspecting area, based on the location of the center 37c of the inspecting area 37b which is displayed on the screen of the monitor 37 when the objective lens which is inserted into the inspecting light path is exchanged with the objective lens 25f for ultraviolet light.

Moreover, the limitation of displacing speed indicates that the displacement of the chucking plate 9 by the operation of the jog handle knob or the eight-direction-displacing button 37f is limited to only the displacement at the low-speed mode, that is, which indicates that switching the speed mode in the two speed modes by a key operation of the keyboard or the displacement speed mode switching button 38 cannot be performed.

In addition, in the state where the objective lens 25f for ultraviolet light is disposed in the inspecting light path, the control PC 33 functions as the displacement controlling device which controls the displacement of the chucking plate 9 based on the control information stored in the memory part 41.

It should be noted that, in the inspecting apparatus 1, before the objective lens 25 is exchanged by the revolving nose piece driving device 27, the chucking plate 9 is displaced in the direction of the Z-axis such that the semiconductor wafer S is distanced from the objective lens 25 by the Z stage 11, thereby preventing contact of the objective lens 25 with the semiconductor wafer S.

Moreover, in the inspecting apparatus 1, after the objective lens 25 which is inserted into the inspecting light path is exchanged, an autofocus operation (AF) is performed, that is, the chucking plate 9 is displaced in the direction of the optical axis L1 by the Z stage, such that the space between the objective lens 25 and the surface Sa of the semiconductor wafer S should be equal to the WD (displacement distance) of the objective lens 25 which is disposed in the inspecting light path.

It should be noted that the concrete AF operations differs in the case in which the visible light objective lenses 25a to 25e and in the case in which the ultraviolet light objective lens 25f, respectively. That is, the focusing in the case in which the visible light objective lenses 25a to 25e is performed automatically through a well-known knife edge method, etc.

On the other hand, the WD of the ultraviolet light objective lens 25f is known beforehand. For this reason, the focusing in the case in which the ultraviolet light objective lens is used is performed as follows, that is, using the visible light objective lenses 25a to 25e, focusing thereof is conducted previously, and then the chucking plate 9 is displaced automatically such that the space between the ultraviolet light objective lens 25f and the surface Sa of the semiconductor wafer S should be equal to the WD of the ultraviolet light objective lens 25f, based on the point where the focusing of the visible light objective lenses 25a to 25e was obtained.

Next, operation of the inspecting apparatus 1 constituted as mentioned above will be explained.

Figure 4:
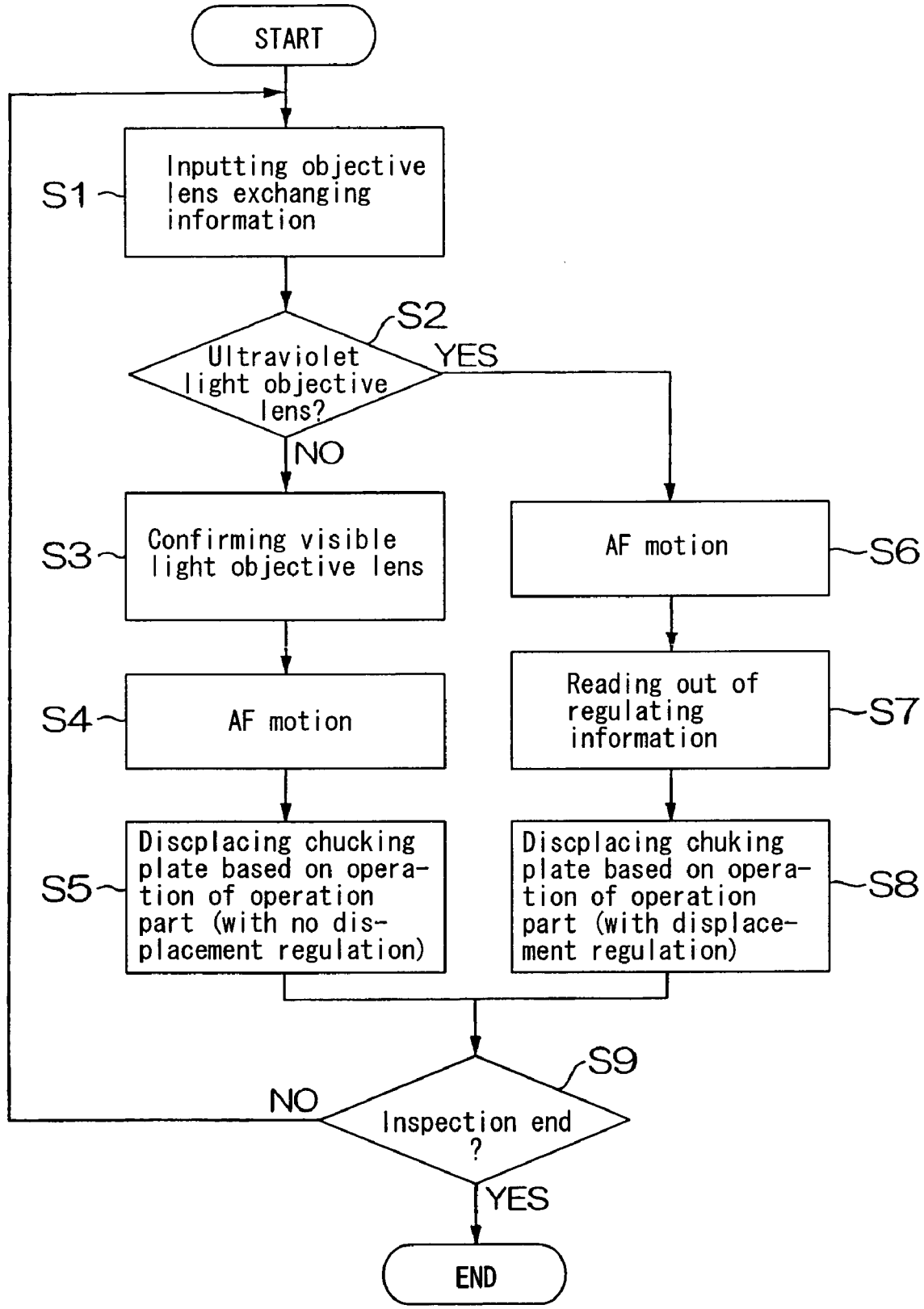
FIG. 4 is a flow chart for explaining operation of the inspecting apparatus shown in FIG. 1.

In the case in which an inspecting of the defects which exist on the surface Sa of the semiconductor wafer S is performed, the semiconductor wafer S to be inspected is first loaded on the chucking plate 9, and the back surface Sb of the semiconductor wafer S is held by a vacuum to the chucking plate 9. Subsequently, as shown in FIG. 4, a direction to exchange the objective lens with a predetermined objective lens 25 in the operating part 39 is inputted (Step S1). At this time, the revolving nose piece driving device 27 rotates the revolving nose piece main body 23, and disposes the predetermined objective lens 25 in the inspecting light path. The control PC 33 recognizes the kind of the predetermined objective lens 25 based on the detected result of the objective lens detecting device 31, and judges whether the predetermined objective lens 25 is the ultraviolet light objective lens 25f or not (Step S2).

Here, when the predetermined objective lens 25 is any one of the visible light objective lenses 25a to 25e, the control PC 33 confirms the kind of the predetermined visible light objective lenses 25a to 25e (Step S3). Then the control PC 33 computes the location where the focusing is attained, corresponding to WD of the visible light objective lenses 25a to 25e, and displaces the chucking plate 9 in the direction of Z-axis to perform an AF operation i.e., the focusing step (step S4).

Thereafter, the operating part 39 is operated, and the inspecting location displacing process, i.e., displacing the chucking plate 9 in the direction of the X-axis and the direction of the Y-axis is performed (Step S5), the inspecting area is displaced to the defect location on the semiconductor wafer S, and magnifying inspection of the defect is performed. It should be noted that the displacement of the chucking plate 9 in Step S5 can be performed at two kinds of movement speed, i.e., at the low-speed mode and the high-speed mode, and the displacing range of the chucking plate 9 is not limited, either. Moreover, in Step S5, the scanning operation is also possible.

On the other hand, in Step S2, when the control PC 33 recognizes that the predetermined objective lens 25 is the ultraviolet light objective lens 25f, an AF operation (focusing step) which matches the semiconductor wafer S with the focal point of the ultraviolet light objective lens 25f is performed similarly to Step S4, based on the value obtained in the AF operation of the objective lens for visible light (Step S6), and the controlling information is read from the memory part 41 (Step S7). Thereafter, the operating part 39 is operated and, the inspecting location displacing process which displaces the chucking plate 9 in the direction of the X-axis and the direction of the Y-axis is performed (Step S8), such that the inspecting area is displaced to the defect location on the semiconductor wafer S, and magnifying inspecting of the defect is performed.

The displacement of the chucking plate 9 in Step S8 is controlled based on the above controlling information. That is, the displacement of the chucking plate 9 by operation of the joy stick or the eight-direction-displacing button 37f is limited to only the displacement at the low-speed mode. Moreover, the displacing range of the jog handle knob and the chucking plate 9 by operation of the mouse is limited by about 10 times of the inspecting area, and the scanning operation is also inhibited.

It should be noted that the displacement of the chucking plate 9 in Step 5 and Step 8 can be performed until the information input of Step S1 is conducted again, or until the inspecting of the defect on the semiconductor wafer S ends (Step S9).

As mentioned above, according to the inspecting apparatus 1, when a magnifying inspecting of a semiconductor wafer is performed using the ultraviolet light objective lens 25f having WD (working distance) which is smaller than those of the objective lenses 25a to 25e, and a high magnifying power, the displacing range and the displacing speed of the ultraviolet light objective lens 25f and of the chucking plate 9 are controlled with respect to the direction of the X-axis and the direction of the Y-axis, and hence it is possible to prevent contact of the semiconductor wafer S with the ultraviolet light objective lens 25f based on the cambering or bending of the semiconductor wafer S loaded on the chucking plate 9.

Moreover, in order to prevent contact of the ultraviolet light objective lens 25f with the semiconductor wafer S, neither a distance sensor which measures the distance between the ultraviolet light objective lens 25f and the semiconductor wafer S nor a whole surface chucking plate which corrects the cambering or bending of the semiconductor wafer S is necessary to be newly disposed, and hence the manufacturing cost of the inspecting apparatus 1 can be reduced.

It should be noted that, in the above embodiment, when the ultraviolet light objective lens 25f is inserted in the inspecting light path, the displacing range and displacing speed of the chucking plate 9 are limited based on the controlling information stored in the memory part; however, this is not restricted, and for example, displacement of the chucking plate 9 by X stages 13 and the Y stage 15 is also possible. In this constitution, in the case in which the ultraviolet light objective lens 25f is selected and the magnifying inspecting of the semiconductor wafer S is performed, contact with the ultraviolet light objective lens 25f and the semiconductor wafer S can be prevented certainly.

Moreover, the displacement controlling of the chucking plate 9 is not limited to the case in which the ultraviolet light objective lens 25f is inserted in the inspecting light path, and may be performed at least in the case in which the objective lens of which WD (working distance) is smaller than the dimension of the cambering or bending of the semiconductor wafer S is selected. That is, in the case in which the cambering or bending of the semiconductor wafer is larger than the WD of the objective lens 25f of which magnifying power is the largest, it is preferred to perform the displacement controlling when the objective lens 25e which has WD being shorter than that of the ultraviolet light objective lens 25f and may cause an interference with the semiconductor wafer is selected.

Furthermore, although the surface Sa of the semiconductor wafer S is matched with the focal point of the objective lens 25 by the AF operation, this is not restricted, and for example, it is also possible to match the surface Sa on the semiconductor wafer S with the focal point of the objective lens 25 by displacing (manual focusing operation) the chucking plate 9 in the direction of the optical axis using the Z stage 11, based on the operation of the operating part 39.

Figure 5:
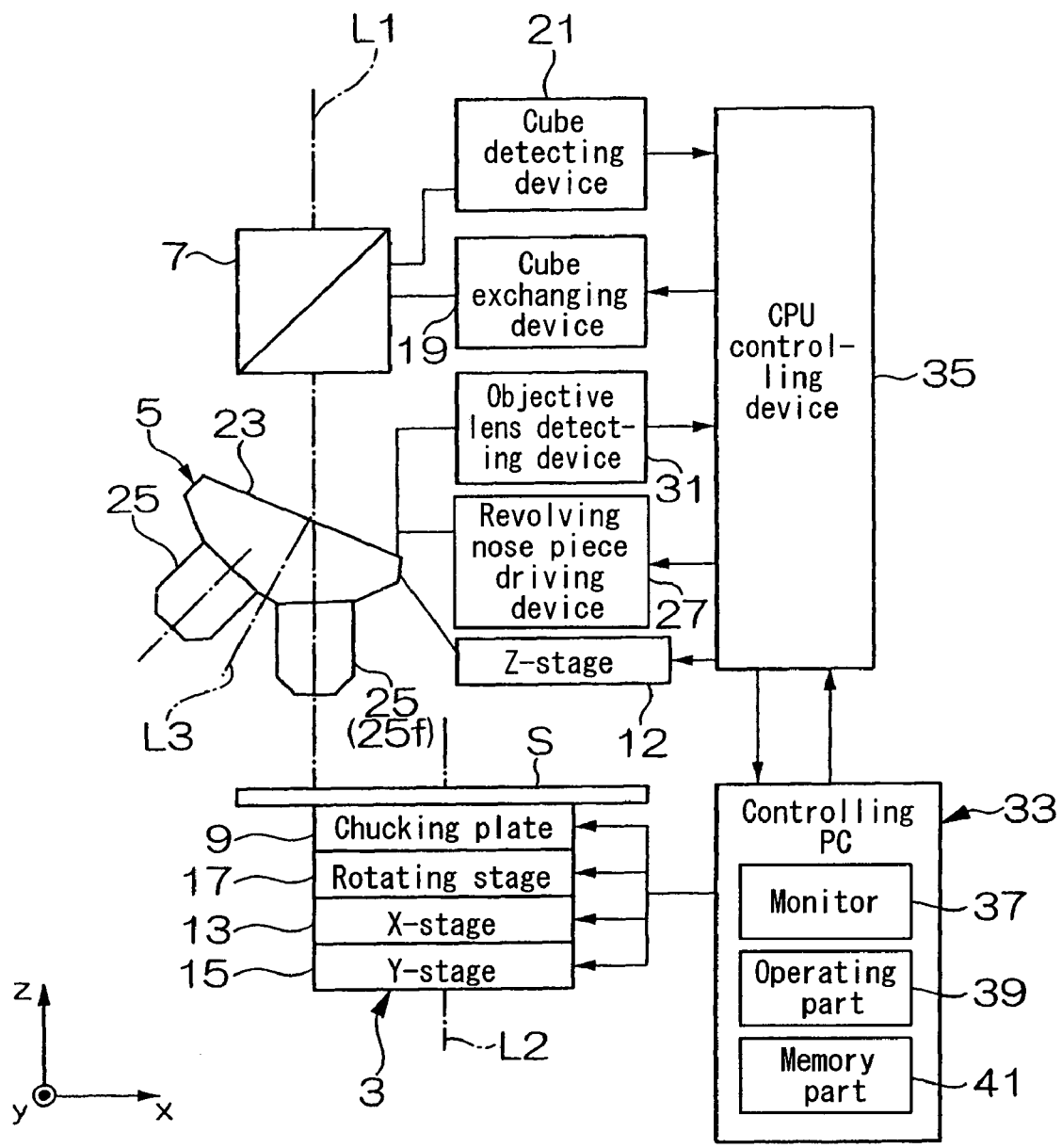
FIG. 5 is a side view showing the schematic constitution of the inspecting apparatus in another embodiment of the present invention.

Moreover, although the sample stage 3 is equipped with the Z stage 11 which displaces the chucking plate 9 in the direction of the Z-axis, this is not restricted, and the objective lens 25 and the chucking plate 9 may be displaced at least with respect to the direction of the Z-axis. That is, for example, as shown in FIG. 5, it is also possible to dispose the Z stage 12 which displaces the revolving nose piece 5 in the direction of the optical axis L1, without disposing the Z stage 11 to the sample stage 3. In this constitution, communication of various information which is exchanged between the Z stage and the control PC 33 such as a location information of the revolving nose piece 5 in the direction of the optical axis L1, displacement information of the revolving nose piece 5, etc., is performed by way of the CPU.

In addition, in controlling or regulating the relative displacement between the objective lens and the loading stage, it may be controlled or regulated at a plural steps of rate and displacement range, depending on the WD (working distance).

According to the inspecting apparatus and the inspecting method of the present invention, when choosing the objective lens of magnification higher than predetermined magnification, i.e., the objective lens of the large magnification whose focal length is smaller than predetermined length, and performing expansion observation of a substrate, relative movement with the objective lens and substrate about the rectangular direction of an optic axis, and since the moving range and movement speed of the rectangular direction of an optic axis are regulated especially, it can avoid that an objective lens and a substrate contact based on the curvature of a substrate, or bending.

Moreover, since there is no necessity of newly preparing the distance sensor which measures the distance of an objective lens and a substrate, the complete chucking plate which corrects curvature and bending of a substrate in order to prevent contact with an objective lens and a substrate, reduction of the manufacture cost of inspecting apparatus can be targeted.

Furthermore, when a move control means forbids relative movement with the objective lens and installation stage by a transportation device according to the inspecting apparatus of this invention, in case the objective lens of high magnification is chosen and expansion observation of a substrate is performed, contact with an objective lens and a substrate can be prevented certainly.

As mentioned above, although the embodiment of the present invention was explained in detail with reference to the drawings, concrete constitution is not restricted to the embodiment, and changes in design in the range which does not deviate from the spirit of the present invention is included.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly and the invention is not to be considered as being limited by the foregoing description, and is only limited by the scope of the appended claims.

What is claimed is:

1. An inspecting apparatus for inspecting a substrate by magnifying a surface of the substrate, comprising:
   an objective lens attaching part equipped with plural objective lenses, each having a different working distance, and which positions one of the objective lenses in an inspecting light path;
   an objective lens exchanging device which actuates the objective lens attaching part to exchange the objective lens which is disposed in an inspecting light path;
   a loading stage which is opposed to the objective lens disposed in the inspecting light path, and on which the substrate is loaded so that the surface of the substrate crosses an optical axis of the inspecting light path substantially rectangularly;
   an objective lens detecting device which determines the working distance of the objective lens disposed in the inspecting light path;
   a displacing device which relatively displaces the objective lens disposed in the inspecting light path and the loading stage in a direction of the optical axis of the inspecting light path and in a direction rectangular to the optical axis; and
   a displacement controlling device to control the relative displacement of the objective lens and the loading stage in the direction rectangular to the optical axis by the displacing device when the lens detecting device detects that the working distance of the objective lens disposed in the inspecting light path is shorter than a predetermined working distance, in order to prevent the objective lens from interfering with the substrate.

2. An inspecting apparatus as set forth in claim 1, wherein the displacement controlling device limits a relative displacing range of the objective lens and the loading stage.

3. An inspecting apparatus as set forth in claim 1, wherein the displacement controlling device limits a relative displacing speed of the objective lens and the loading stage to a speed lower than a predetermined speed.

4. An inspecting apparatus as set forth in claim 1, wherein the displacement controlling device inhibits the relative displacement with the objective lens and the loading stage.

5. An inspecting apparatus as set forth in claim 1, wherein the displacement controlling device stores controlling information which controls the displacement of the loading stage.

6. An inspecting apparatus as set forth in claim 1, wherein the objective lens attaching part comprises a revolving nose piece which exchanges the objective lens by revolving the objective lens around a revolving axis.

7. An inspecting apparatus as set forth in claim 2, wherein the displacement controlling device limits the relative displacing range is limiting an inspecting area of a displacing area of the loading stage, based on the center position of the inspecting area which is displayed on a screen of a monitor when the objective lens to be inserted in the inspecting light path is exchanged with an objective lens having a working distance shorter than the predetermined working distance.

8. An inspecting apparatus as set forth in claim 1, wherein the displacing device has both a high speed mode which is used when the inspecting is performed while displacing from one circuit pattern to another circuit pattern, and a low speed mode which is used when the inspecting is performed while displacing in one circuit pattern.

9. An inspecting apparatus as set forth in claim 8, wherein the displacement controlling device limits the displacement of the loading stage only to the displacement in the low speed mode.

10. A method of inspecting a substrate by performing magnifying inspection of a surface of the substrate via a selected one of a plurality of objective lenses having differing working distances, the method comprising:
    relatively displacing the selected objective lens and the substrate in a direction of an optical axis of the objective lens which crosses the surface of the substrate substantially rectangularly, such that the surface of the substrate is positioned at a focal point of the objective lens;
    relatively displacing the objective lens and the substrate in a direction rectangular to the optical axis, so as to change a magnifying inspecting point on the surface of the substrate; and
    controlling the relative displacement of the objective lens and the substrate when the selected objective lens has a working distance that is shorter than a predetermined working distance, in order to prevent the objective lens from interfering with the substrate.

* * * * *

UNITED STATES PATENT AND TRADEMARK OFFICE
CERTIFICATE OF CORRECTION

PATENT NO.        : 7,456,947 B2                                    Page 1 of 1
APPLICATION NO. : 11/078084
DATED             : November 25, 2008
INVENTOR(S)       : Shunsuke Kurata It is certified that error appears in the above-identified patent and that said Letters Patent is hereby corrected as shown below:

Column 12, line 13, (Claim 7, line 3);

Change "is" to --by--.

Signed and Sealed this

Twenty-fourth Day of February, 2009

JOHN DOLL
*Acting Director of the United States Patent and Trademark Office*